United States Patent [19]

Biermann et al.

[11] Patent Number: 4,748,158

[45] Date of Patent: May 31, 1988

[54] ALKYL GLYCOSIDES AS POTENTIATING AGENTS IN ANTISEPTIC, DISINFECTING AND CLEANING PREPARATIONS TO INCREASE MICROBICIDAL ACTIVITY

[75] Inventors: Manfred Biermann, Muelheim; Rudolf Lehmann; Harald Schnegelberger, both of Leichlingen; Walter Ploeger, Hilden; Hans-Juergen Klueppel, Duesseldorf; Karl-Heinz Schmid, Mettmann, all of Fed. Rep. of Germany

[73] Assignee: Henkel Kommanditgesellschaft auf Aktien, Duesseldorf, Fed. Rep. of Germany

[21] Appl. No.: 806,059

[22] Filed: Dec. 6, 1985

[30] Foreign Application Priority Data

Dec. 10, 1984 [DE] Fed. Rep. of Germany ....... 3444958

[51] Int. Cl.$^4$ ..................... A61K 31/70; A61K 7/16
[52] U.S. Cl. ..................................... 514/25; 514/49; 514/635

[58] Field of Search ............................ 514/25, 635, 49; 536/4.1, 16.8

[56] References Cited

U.S. PATENT DOCUMENTS

| | | | |
|---|---|---|---|
| 2,684,924 | 7/1954 | Rose et al. | 514/635 |
| 3,772,269 | 11/1973 | Lew | 536/4.1 |
| 4,053,636 | 10/1977 | Eustis, III et al. | 514/635 |
| 4,395,405 | 7/1983 | Noda et al. | 514/25 |

FOREIGN PATENT DOCUMENTS 2364860  7/1974  Fed. Rep. of Germany ..... 536/16.8

Primary Examiner—J. R. Brown
Assistant Examiner—Elli Peselev
Attorney, Agent, or Firm—Ernest G. Szoke; Henry E. Millson, Jr.

[57] ABSTRACT

Alkyl glycosides are used to greatly increase the microbicidal activity of biguanide compounds, such as chlorhexidine salts. The alkyl glycoside/biguanide agents have a particular utility in teeth cleaning preparations due to their improved microbicidal activity against gram-positive bacteria.

28 Claims, No Drawings

ALKYL GLYCOSIDES AS POTENTIATING AGENTS IN ANTISEPTIC, DISINFECTING AND CLEANING PREPARATIONS TO INCREASE MICROBICIDAL ACTIVITY

BACKGROUND OF THE INVENTION

1. Field of the Invention

The present invention relates to potentiated microbiocidal agents and more particularly relates to antiseptic biguanide compositions potentiated with alkyl glycosides having applications in the oral health field.

2. Description of Related Art

Alkyl glycosides, their production and their use, particularly as surfactants, have been known for some time. See, for example, U.S. Pat. Nos. 3,839,318; 3,772,269; 3,707,535 and 3,547,828; German patent Nos. 1,905,523; 1,943,689; 2,036,472 and 3,001,064; and also European patent No. 77,167. Alkyl glycosides are typically produced by reacting glucose or oligosaccharides with alcohols containing from 8 to 25 carbon atoms and more particularly with alcohols containing from 10 to 18 carbon atoms. Alkyl glycosides have been used in a variety of commercial applications particularly as biodegradable surfactants.

Investigations into the microbiological activities of alkyl glycosides have shown that they exhibit no significant antimicrobial activity even at concentrations as high as 10,000 ppm. Furthermore, combinations of alkyl glycosides with quaternary ammonium compounds are similarly undistinguished in their antimicrobial effect. While quaternary ammonium compounds exhibit bactericidal activity, their use with an alkyl glycoside surfactant, as described, for example, in U.S. Pat. No. 3,547,828, produces no increased or unexpected bactericidal effect.

DESCRIPTION OF THE INVENTION

It has now been surprisingly discovered that alkyl glycosides, in combination with selected antimicrobial agents, produce synergistic improvements in the antimicrobial performance of the antimicrobial agents. In particular embodiments of the invention, the activity of antimicrobial agents against gram-positive bacteria is distinctly improved by combining them with alkyl glycosides.

Accordingly, the present invention relates to the use of alkyl glycosides as potentiating agents for increasing the microbiocidal activity of bactericidally active biguanide compounds, especially microbiocidal activity against gram-positive bacteria, in antiseptic preparations. More particularly, the present invention pertains to bactericidal disinfecting and cleaning preparations comprising in combination, an alkyl glycoside and a microbiocidal biguanide, having particular utility in personal hygiene preparations, such as oral and dental hygiene preparations, for example, toothpastes, tooth powders and mouthwashes.

As examples of the microbiocidal agents which can be used in combination with the alkyl glycosides according to the present invention there can be mentioned antiseptic biguanide compounds, such as chlorhexidine (which is the common name for the antiseptic 1,1'-hexamethylene-bis-[5-(4-chlorophenyl)-biguanide], widely used in the form of its salts (such as the acetate, hydrochloride, and gluconate salts) in the cosmetic and pharmaceutical fields and also in cleaning preparations). Other known biguanide-based disinfectants are, for example, the salts of polyhexamethylene biguanide compounds having the following general formula

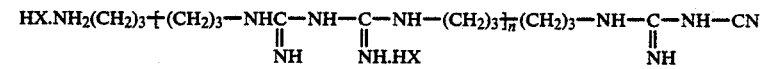

in which HX is the salt-forming acid component, such as HCl, for example, and n is a number having a value of at least 2, and preferably having a value of from about 4.5 to 6.5.

Numerous antimicrobial biguanide compounds which can be used in the present invention are mentioned in the patent literature, including, for examples, European Patent No. 24,031; U.S. Pat. Nos. 2,684,924; 2,990,425; 3,468,898; 4,022,834 and 4,053,636; and German patent Nos. 2,212,259 and 2,627,548. Additional examples of antimicrobial biguanide compounds which can be utilized in the present invention include $N^1$-(4-chlorobenzyl)-$N^5$-(2,4-dichlorobenzyl)-biguanide; p-chlorophenyl biguanide; 4-chlorobenzhydryl biguanide; N-3-lauroxypropyl-$N^5$-p-chlorobenzyl biguanide; $N^1$-p-chlorophenyl-$N^5$-lauryl biguanide and the non-toxic addition salts thereof, especially gluconates and acetates.

The surprising improvement in activity obtained in accordance with the invention is apparent, for example, from the following figures: 250 ppm of chlorhexidine gluconate in aqueous solution (the water having a hardness of 17° dH (German hardness) at a temperature of 20° C.) is unable to kill a suspension of *Staphylococcus aureus* bacteria within one hour's time. By adding 0.1% (1000 ppm) of an alkyl glycoside to the aqueous solution, the *Staphylococcus aureus* bacteria is completely killed in 15 minutes with only a 50 ppm concentration of chlorhexidine gluconate. This synergistic bactericidal activity also is obtained against other bacteria, such as the *Streptococcus faecium*. Thus, utilizing the potentiated microbiocidal compositions of the present invention makes it possible to use far lower microbiocidal agent concentrations while at the same time, obtaining satisfactory microbiocidal activity, particularly against gram-positive bacteria.

In the field of oral and dental care, it is particularly important to provide microbiocidal activity against gram-positive bacteria since it is known that gram-positive bacteria contribute to the formation of plaque leading to tooth caries. Unfortunately to date, the types of bactericidal agents used in toothpastes have failed to effectively prevent plaque from forming, at the agent concentrations permitted by regulation. It is possible, utilizing the microbiocidal agents of the present invention, to provide far more effective teeth cleaning preparations having improved microbiocidal activity against gram-positive bacteria than has hitherto been available, without any need to increase the concentration of the microbiocidal agents used.

Although the present invention is not limited to any particular weight ratio range of alkyl glycoside-to-bactericidally active biguanide component, the alkyl glycosides are generally used in at least substantially the same quantity by weight as the bactericidally active components. Usually the amount of alkyl glycoside present in the composition is above about 10 ppm, preferably above about 50 ppm. Particularly preferred concentrations of alkyl glycosides used in the microbiocidal compositions of the present invention are in the range of 10–2000 ppm, more preferably 50–1000 ppm. In conjunction with the biguanide compound alkyl glycoside concentrations of from about 50 to 500 ppm are particularly preferred. However, suitable ranges for particular purposes may be determined by simple tests well known to those of ordinary skill in this art. In some cases, it may be desirable to use comparatively small amounts of the alkyl glycosides. On the other hand, the alkyl glycosides may also be used in a considerable weight excess in relation to the amount of the bactericidally active component. This has particular significance in certain embodiments of the invention described in more detail hereinafter, including synergistic improvement in bactericidal activity of disinfecting and cleaning preparations, especially preparations used in the field of oral and dental hygiene.

The alkyl glycoside potentiating agents utilized in accordance with the present invention may be derived using known procedures from fatty alcohols and sugars. Preferred glycosides include those containing an alkyl group selected from $C_6$, $C_8$, $C_{10}$, $C_{12}$, $C_{14}$, $C_{16}$ and $C_{18}$ alkyl groups. With respect to the present invention, these groups may be linear or branched, saturated or mono- or poly-olefinically unsaturated and may contain, for example, up to 3 double bonds. The alkyl glycosides of the present invention may also comprise mixtures of one or more of the glycosides mentioned above. Expecially preferred alkyl glycosides include those wherein the alkyl group contains from 8 to 16 carbon atoms and, more preferably, from 10 to 14 carbon atoms.

So far as the saccharide moiety of the glycosides is concerned, both alkyl monoglycosides, in which a cyclic sugar residue is attached to the fatty alcohol, and also alkyl oligoglycosides preferably containing no more than 8 and, and more preferably, no more than 3 glycosidically bound glucose or maltose residues are suitable. The above recited ranges for the number of sugar residues (i.e., the degree of oligomerization) is a statistical mean value based on the average distribution for these compounds. Alkyl glycosides containing $C_{10}$–$C_{14}$ fatty alcohols in the alkyl group(s) and up to 2 glycoside residues and preferably up to 1.5 glycoside residues are particularly suitable.

Procedures for preparing the alkyl glycoside component of the present invention are well known, as for example illustrated in U.S. Pat. No. 3,598,865. For example, the Fisher process of producing alkyl mono glycosides involves heating glucose and a lower alcohol with an acid catalyst. Other procedures are also known.

One important application of the bactericidal agents of the present invention is in personal hygiene preparations and, more particularly, in oral and dental disinfecting and cleaning preparations. Typical compositions of dental cleaning preparations are disclosed, for example, in German patent Nos. 2,212,259 and 2,627,548. These preparations typically contain from about 0.01% to about 5% by weight and preferably no more than about 2.5% by weight of the microbiocidal biguanide compounds. The biguanide compounds are preferably added in quantities of from about 0.03 to about 1.2% by weight and, more particularly, in quantities of from about 0.05 to about 0.8% by weight, all these figures being based on the total weight of the preparation.

As mentioned above, in the present invention the alkyl glycosides are present in combination with the biguanide compounds, preferably in at least substantially equivalent quantities (by weight) or, if desired, even in considerable excess quantities. Since alkyl glycosides are known surfactants, they also perform the known foaming functions of surfactants, for example in toothpastes or tooth powders, in which case they can be used in a quantity that both meets the requirements of a "bactericidal potentiating" function and the requirement of a "surfactant foaming" function.

The pH of personal hygiene preparations of the type in question is preferably in the range of from about 4.5 to 9.5 and more preferably in the range of from about 6 to 8. The microbiocidal agents of the present invention may be used in conjunction with any suitable carrier performing a known function in personal hygiene preparations of the type in question. The carrier in oral and/or dental hygiene preparations may be, for examples, a standard toothpaste, mouthwash, chewing gum or the like.

Dental care and tooth cleaning preparations usually also contain abrasive polishes, foaming agents, flavorings and sweeteners. In addition, toothpastes generally contain humectants, binders and water. Known, suitable polishes include, for example, calcium carbonate, dicalcium orthophosphate dihydrate, calcium pyrophosphate, calcium polymetaphosphate, insoluble sodium polymetaphosphate, aluminum trihydroxide, α-aluminum oxide and silicas, particularly gel silicas and precipitated silicas. It is preferred to use abrasives which are compatible with the biguanide compounds.

The total content of abrasives in teeth cleaning preparations may amount to between about 0.5 to 95% by weight, based on the total weight of the tooth cleaning preparation. The abrasives are normally present in quantities of from about 6 to 60% by weight in toothpastes and in quantities of from about 20 to about 95% by weight in tooth powders.

Teeth cleaning preparations also normally contain surfactants as foaming agents. Suitable surfactants include well-known non-soap-like, nonionic, cationic, zwitter-ionic and amphoteric organic synthetic surfactants. As already mentioned, however, the alkyl glycosides used in accordance with the bactericidal potentiating function of the present invention are particularly suitable. Suitable non-ionic detergents include condensates of alkylene oxides, e.g., ethylene oxide, with organic hydrophobic compounds containing, for example, an aliphatic or alkyl aromatic group including for example propylene oxide condensates of propylene glycol and sorbitan monostearate. The foaming agents are normally used in quantities of from about 0.5 to 5% by weight in tooth cleaning and dental-care preparations.

Suitable flavorings include, for examples, methyl salicylate, peppermint oil, sassafras oil and aniseed oil. The flavorings are generally used in quantities of from about 0.01 to 2.0% by weight. Sweeteners may be used in quantities of from about 0.05 to about 2% by weight.

Thickeners are also frequently added to toothpastes in quantities of from about 0.1 to 5.0% by weight, based on the total weight of the toothpaste. Suitable thickeners include hydroxyethyl cellulose and water-soluble salts of cellulose ethers, natural gums, mucilages and colloidal inorganic components, such as finely divided silicon dioxide and colloidal magnesium aluminum silicate.

Suitable humectants include, for examples, glycerine, sorbitol and other polyhydric alcohols, and mixtures thereof. The humectants may be present in quantities of from about 1 to 50% by weight, based on the total weight of the toothpaste, and are generally present in admixture with water.

Mouthwashes generally contain a water/ethyl alcohol solution and, if desired, components such as flavorings, sweeteners and humectants of the type mentioned above. In accordance with the present invention, the above-described combination of microbiocidal biguanide compounds and alkyl glycosides may be added to mouthwashes in order to achieve the advantages of the present invention.

It is important, however, to note that the presence of other components, particularly surfactants and/or emulsifiers in the microbicidal agents of the present invention may decrease the potentiating effect of the alkyl glycosides, even to the point where they may become totally ineffective in their potentiating ability. Accordingly, the appropriate mixing range for the components present in each individual case should always be determined by the preliminary routine tests. It is therefore preferred that the alkyl glycosides, which themselves have surfactant properties be used in an amount sufficient to provide the necessary degree of foaming so that the quantity of other surfactants or emulsifiers may readily be limited.

The following Examples illustrate particular advantages of the present invention. Those skilled in the art will appreciate that these examples are merely illustrative of, but do not in any way limit, the scope of the present invention which is defined in the appended claims.

EXAMPLES

A. Microbiocidal Activity

The microbicidal activities of the biguanide/alkyl glycoside compositions of the present invention were determined against the following test microbe suspensions:

| (A) Staphylococcus aureus | $2 \times 10^9$ cells/ml |
| (B) Streptococcus faecium | $2 \times 10^9$ cells/ml |
| (C) Streptococcus mutans | $1 \times 10^9$ cells/ml |
| (D) Escherichia coli | $2 \times 10^9$ cells/ml |
| (E) Candida albicans | $2 \times 10^8$ cells/ml |

The time required for the microbiocidal agents to completely destroy the cells in the microbe suspension was determined according to the following procedures. Using water having a hardness of 17° dH (German hardness), test solutions were prepared containing alkyl glycoside concentrations of 1000 and 100 ppm and chlorhexidine gluconate (1,1'-hexamethylene-bis-[5(4-chlorophenyl)-biguanide]-gluconate) concentrations of 500, 250, 100, 50 and 25 ppm. In addition, two groups of comparison solutions were prepared which contained (1) only chlorhexidine gluconate in the five concentrations indicated and; (2) only the respective alkyl glycosides at a concentration of 10,000 ppm.

Small quantities (0.1 ml) of the test microbe suspensions at room temperature were pipetted into test tubes and mixed with 10 ml quantities of the test or comparison solutions described above. After contact times ranging up to 60 minutes, approximately a 0.05 ml quantity of liquid was removed from each test tube by means of an inoculating ring and spread onto nutrient agar containing 3% TWEEN 80 TM (Atlas Chemical Industries, Inc., Wilmington) and 0.3% lecithin. The nutrient medium consisted of 2.5% by weight Standard-I-Bouillon (Merck & Co., Inc., Rahway, N.J.) for microbe suspensions A through D and Wurzebouillon pH 5 (Merck & Co., Inc.) for microbe suspension E. Both nutrient mediums contained 1.2 wt % agar for gelatinization. The samples were incubated at 37° C. and 30° C., respectively. After a minimum incubation period of 3 days, the cultures were macroscopically examined for microbial growth, and the destruction time and residual cell content determined in this way.

In Tables I and II, "+" means that there were less than 50 residual microbe cells after a contact time of 60 minutes; "++" means that there were less than 200 residual microbe cells after a contact time of 60 minutes; and "+++" means that there were more than 200 residual microbe cells after a contact time of 60 minutes. The numerical values in the individual Table columns are contact times required for a complete kill of the microbes in minutes at the indicated dosage.

EXAMPLE 1

The following alkyl glycosides Nos. 1 to 6 were each used in a concentration of 1000 ppm together with the quantities of chlorhexidine gluconate indicated in Table I:

(1) A $C_8$–$C_{10}$ alkyl oligoglucoside (having a degree of oligomerization of 1.8) in which the alkyl groups were derived from an n-octanol/n-decanol mixture having a weight ratio of 60:40.

(2) a $C_8$–$C_{10}$ alkyl oligoglucoside (having a degree of oligomerization of 1.8) in which the alkyl groups were derived from an n-octanol/n-decanol mixture having a weight ratio of 40:60.

(3) a $C_8$–$C_{10}$ alkyl oligoglucoside (having a degree of oligomerization of 1.3) in which the alkyl groups were derived from an n-octanol/n-decanol mixture having a weight ratio of 50:50.

(4) a $C_{12}$–$C_{14}$ alkyl monoglucoside in which the alkyl groups were derived from an n-dodecanol/n-tetradecanol mixture having a weight ratio of 70:30.

(5) a $C_{12}$–$C_{14}$ alkyl oligoglucoside (having a degree of oligomerization of 1.5) in which the alkyl groups were derived from an n-dodecanol/n-tetradecanol mixture having a weight ratio of 70:30.

(6) a $C_{12}$–$C_{14}$ alkyl oligoglucoside (having a degree of oligomerization 1.4) in which the alkyl groups were derived from an n-dodecanol/n-tetradecanol mixture having a weight ratio of 70:30.

The solutions were tested against microbe suspensions A, B and C. The results obtained are presented in Table I below. The effect of the chlorhexidine gluonate solutions alone (i.e., without the addition of any alkyl glycoside) is presented in the first column labeled "0". The effect of the glycoside solutions alone at a concentration of 10,000 ppm (i.e., without the addition of any chlorhexidine gluconate) is presented in the three rows labeled "0".

TABLE 1

| Chlorhexidine Gluconate Concentration (ppm) | 0 | 1 | 2 | 3 | 4 | 5 | 6 |
|---|---|---|---|---|---|---|---|
| *Staphylococcus aureus* | | | | | | | |
| 500 | 60 | — | — | — | — | — | — |
| 250 | + | — | — | — | $\leq 15$ | $\leq 15$ | $\leq 15$ |
| 100 | +++ | 15 | $\leq 5$ | $\leq 5$ | 60 | $\leq 15$ | $\leq 15$ |
| 50 | — | 15 | $\leq 5$ | $\leq 5$ | + | 60 | $\leq 15$ |
| 25 | — | 15 | 15 | $\leq 5$ | — | — | — |
| 0 | | + | + | + | +++ | +++ | +++ |
| *Streptococcus faecium* | | | | | | | |
| 500 | ++ | — | — | — | — | — | — |
| 250 | +++ | — | — | — | $\leq 15$ | $\leq 15$ | $\leq 15$ |
| 100 | +++ | $\leq 5$ | $\leq 5$ | $\leq 5$ | 60 | $\leq 15$ | $\leq 15$ |
| 50 | — | $\leq 5$ | $\leq 5$ | $\leq 5$ | +++ | 60 | $\leq 15$ |
| 25 | — | $\leq 5$ | 15 | $\leq 5$ | — | — | — |
| 0 | | +++ | +++ | +++ | +++ | +++ | +++ |
| *Streptococcus mutans* | | | | | | | |
| 500 | ++ | — | — | — | — | — | — |
| 250 | ++ | — | — | — | — | — | $\leq 15$ |
| 100 | +++ | 60 | 60 | 60 | — | — | 60 |
| 50 | — | 60 | 60 | 60 | — | — | 60 |
| 25 | — | 60 | 60 | 60 | — | — | — |
| 0 | | ++ | ++ | ++ | — | — | ++ |

EXAMPLE 2

The following alkyl glycosides Nos. 7 to 10 were each used in a concentration of 100 ppm together with the quantities of chlorhexidine gluconate indicated in Table II:

(7) a $C_{12}$–$C_{14}$ alkyl oligoglucoside (having a degree of oligomerization of 1.4) in which the alkyl groups were derived from an n-dodecanol/n-tetradecanol mixture having a weight ratio of 70:30.

(8) a $C_{12}$–$C_{14}$ alkyl oligoglucoside (having a degree of oligomerization of 1.7) in which the alkyl groups were derived from an n-dodecanol/n-tetradecanol mixture having a weight ratio 70:30.

(9) a dodecyl monoglucoside

(10) an undecenyl monoglucoside

The solutions were tested against microbe suspensions A, D and E. The results obtained are presented in Table II below. The results of the chlorhexidine gluconate solutions alone (i.e., without the addition of any glucoside) are presented in the column of the Table labeled "0". The results of the glycoside solution alone at a concentration of 10,000 ppm (i.e., without the addition of any chlorhexidine gluconate) are presented in the three rows labeled "0". The general observations made with respect to Table I apply to Table II as well.

TABLE II

| Chlorhexidine Gluconate Concentration (ppm) | Aliphatic Glycoside No. | | | | |
|---|---|---|---|---|---|
| | 0 | 7 | 8 | 9 | 10 |
| *Staphylococcus aureus* | | | | | |
| 500 | 60 | — | — | — | — |
| 250 | ++ | — | — | — | — |
| 100 | +++ | 15 | 15 | 15 | 60 |
| 50 | — | 15 | 15 | 15 | 60 |
| 25 | — | 60 | 15 | 15 | ++ |
| 0 | | +++ | +++ | +++ | ++ |
| *Escherichia coli* | | | | | |
| 500 | 15 | — | — | — | — |
| 250 | 15 | — | — | — | — |
| 100 | 60 | $\leq 5$ | $\leq 5$ | $\leq 5$ | $\leq 5$ |
| 50 | ++ | 60 | 60 | 60 | 15 |
| 25 | — | +++ | ++ | + | 60 |
| *Candida albicans* | | | | | |
| 500 | $\leq 5$ | — | — | — | — |
| 250 | 15 | — | — | — | — |
| 100 | 60 | $\leq 5$ | 15 | 15 | 15 |
| 50 | + | 60 | 60 | 15 | 60 |
| 25 | ++ | 60 | + | 60 | 60 |
| 0 | | 60 | 60 | +++ | +++ |

B. Effectiveness in Surface Disinfection

EXAMPLE 3

The effectiveness of the combination of a biguanide compound and an alkyl glycoside according to the present invention as a surface disinfectant was determined in accordance with the guidelines for testing chemical disinfecting agents set forth by the German Association of Hygiene and Microbiology, described in Hygiene & Medizin 9 (1984), pp. 42–43.

The test microbe suspension contained *Staphylococcus aureus* in a concentration of $2 \times 10^9$ cells/ml.

Solutions A and B, both containing 500 ppm of chlorhexidine gluconate and 1000 ppm of isotridecyloligoglucoside (degree of oligomerization 1.5), were used as disinfecting agents according to the invention. Solution B additionally contained 1000 ppm of an adduct of 5 moles ethylene oxide and 4 moles propylene oxide with a $C_{12}$–$C_{14}$ fatty alcohol (composition in percentages by weight: 0–2 $C_{10}$; 70–75 $C_{12}$; 25–30 $C_{14}$; 0–2 $C_{16}$). Solutions A and B were tested against water having a hardness of 17° dh (i.e., water of standardized hardness hereinafter "WSH") and also tested against a comparison solution C which contained only 500 ppm of chlorhexidine gluconate.

The test surfaces comprised $50 \times 50$ mm pieces of flexible PVC floor covering made in accordance with DIN 16 951 (April 1977 edition). Before contamination, the test surfaces were wiped first with water, then with ethanol (70% by volume) and dried.

A 0.1 ml quantity of test microbe suspension was applied by pipette to each test surface and uniformly distributed with a glass spatula over the central area measuring 30×30 mm (edge length). After drying the microbe suspension for a period of 90 minutes, 0.2 ml quantities of the above-identified solutions were applied to the test surfaces using a glass spatula.

After contact times of 15 mins. and 60 mins., the PVC pieces were introduced into sealable 200 ml containers containing 100 ml of a casein-soya-peptone solution having 3% by weight of Tween TM 80 and 0.3% by weight of lecithin and glass beads. To free the microbes, the containers were shaken for 2 mins. in a shaking machine. Thereafter, two dilutions ($10^{-2}$ and $10^{-4}$) were prepared from each of the liquid obtained. Small quantities (0.1 ml) of both the undiluted liquid and the two dilutions were applied by spatula to a plate of casein-soya-peptone-agar containing 3% by weight of Tween TM 80 and 0.3% by weight of lecithin. The agar plates were incubated at 37° C. After a minimum incubation period of 2 days, the number of colony-forming units (CFU) was determined.

Table III below presents the reduction in microbe count ($MR_t$) obtained with the individual solutions for a time t (in this case, t is either 15 or 60 mins) by comparison with WSH. The microbe reduction is calculated in accordance with the equation:

$$MR_t = \log CFU (WSH) + \log CFU (D)$$

in which CFU (WSH) represents the number of colony-forming units after the action of WSH and CFU (D) represents the number of colony-forming units after the action of the disinfectant solution.

| Disinfectant Solutions: | | $MR_{15}$ | $MR_{60}$ |
|---|---|---|---|
| (A) | 500 ppm chlorhexidine gluconate<br>1000 ppm isotridecyloligoglucoside | 3.0 | 3.7 |
| (B) | 500 ppm chlorhexidine gluconate<br>1000 ppm isotridecyloligoglucoside<br>1000 ppm fatty alcohol-ethylene oxide-propylene oxide adduct | 2.4 | 3.0 |
| (C) | 500 ppm chlorhexidine gluconate | 2.1 | 2.4 |

We claim:

1. A microbiocidal composition comprising a microbiocidally-active combination of a biguanide compound microbiocidally active against bacteria and from about 10 to about 10,000 ppm of a $C_6$-$C_{18}$-alkyl glycoside in a non-microbiocidally-active amount which is sufficient to potentiate the microbiocidal activity of said biguanide.

2. The composition as defined in claim 1, wherein the biguanide compound comprises a chlorhexidine salt.

3. The composition as defined in claim 1, wherein the amount of alkyl glycoside is in the range of about 10-2000 ppm.

4. The composition as defined in claim 1, wherein the amount of alkyl glycoside is in the range of about 50-1000 ppm.

5. The compositon as defined in claim 1, wherein the alkyl glycoside and the biguanide compound are present in substantially the same quantities by weight.

6. The composition as defined in claim 1, wherein the alkyl glycoside contains an alkyl group having from about 8 to 16 carbon atoms.

7. The composition as defined in claim 6, wherein the alkyl group contains from about 10 to 14 carbon atoms.

8. The composition as defined in claim 1, wherein the alkyl glycoside comprises a monoglycoside.

9. The composition as defined in claim 1, wherein the alkyl glycoside comprises an oligoglycoside.

10. The composition as defined in claim 9, wherein the oligoglycoside contains up to 8 glycoside residues.

11. The composition as defined in claim 9, wherein the oligoglycoside contains up to 3 glycoside residues.

12. A surface disinfection composition including the microbiocidal composition of claim 1.

13. A hygienic composition for the care of the oral cavity comprising a physiologically-compatible carrier and the microbiocidal composition of claim 1 in a microbiocidally-active amount.

14. The hygienic composition of claim 13, further including an abrasive tooth polish compatible with the biguanide compound.

15. The hygienic composition of claim 13, wherein the carrier comprises a solution of alcohol in water.

16. The hygienic composition of claim 13, further including a binder.

17. The hygienic composition of claim 13, wherein the microbiocidal composition comprises a biguanide compound present in a amount insufficient for substantial microbiocidal activity, and the $C_6$-$C_{18}$- alkyl glycoside is present in an amount sufficient to potentiate the microbiocidal activity of the biguanide compound and microbiocially-activate the microbiocidal composition.

18. The hydienic composition of claim 17, further including an abrasive tooth polish compatible with the biguanide compound.

19. The hygienic composition of claim 13, wherein the bacteria are gram-positive bacteria.

20. The hygienic composition of claim 13, wherein the alkyl glycoside is present in an amount sufficient to further function as a foaming agent.

21. The composition of claim 1, wherein the alkyl glycoside is the reaction product of a fatty alcohol and a sugar.

22. The composition of claim 1, wherein the alkyl portion of the glycoside contains an even number of carbon atoms.

23. A method for improving the hygiene of the oral cavity comprising contacting the cavity with a hygienic composition according to claim 13.

24. The method of claim 23, wherein the bacteria are gram-positive bacteria.

25. The method of claim 24, wherein the microbicidally-active

26. The method of claim 24, wherein the microbiocidally-active composition is a tooth powder.

27. The method of claim 24, wherein the microbiocidally-active composition is a mouthwash.

28. The method of claim 23, wherein the biguanide compound is present in an amount insufficient for substantial microbiocidal activity in the oral cavity and the $C_6$-$C_{18}$-alkyl glycoside is present in an amount sufficient to potentiate the microbiocidal activity of the biguanide compound and to microbiocidally activate the composition.

* * * * *

UNITED STATES PATENT AND TRADEMARK OFFICE
CERTIFICATE OF CORRECTION

PATENT NO. : 4,748,158
DATED : May 31, 1988
INVENTOR(S) : Manfred Biermann et al.

It is certified that error appears in the above-identified patent and that said Letters Patent is hereby corrected as shown below:

In claim 18, at col. 10, line 34, delete "hydienic" and add --hygienic--.

In claim 25, at col. 10, line 54, after "-active", read --composition is a toothpaste--.

Signed and Sealed this

Twenty-second Day of May, 1990

Attest:

HARRY F. MANBECK, JR.

*Attesting Officer*

*Commissioner of Patents and Trademarks*